United States Patent [19]

Eisele

[11] Patent Number: 5,159,834
[45] Date of Patent: Nov. 3, 1992

[54] DEVICE FOR OPTOELECTRONIC INTERFACE MEASUREMENT AND REFRACTOMETRY IN LIQUIDS

[75] Inventor: Ronald Eisele, Daenisch-Nienhof, Fed. Rep. of Germany

[73] Assignee: Fibronix Sensoren GmbH, Kiel, Fed. Rep. of Germany

[21] Appl. No.: 679,684

[22] Filed: Apr. 4, 1991

[30] Foreign Application Priority Data

Apr. 5, 1990 [DE] Fed. Rep. of Germany ....... 4010948

[51] Int. Cl.$^5$ .............................................. G01F 23/28
[52] U.S. Cl. ...................... 73/293; 250/577; 340/619
[58] Field of Search .......................... 73/293; 340/619; 250/577

[56] References Cited

U.S. PATENT DOCUMENTS

| | | | |
|---|---|---|---|
| 3,808,887 | 5/1974 | Buttriss | 73/293 |
| 4,038,650 | 7/1977 | Evans et al. | 73/293 X |
| 4,711,126 | 12/1987 | Houpt et al. | 250/577 X |
| 4,840,137 | 6/1989 | Beauvais et al. | 73/293 X |
| 4,873,863 | 10/1989 | Bruhl et al. | 73/293 |
| 5,054,319 | 10/1991 | Fling | 73/293 |

FOREIGN PATENT DOCUMENTS

| | | | |
|---|---|---|---|
| 0039187 | 4/1981 | European Pat. Off. | 73/293 |
| 3243839 | 5/1984 | Fed. Rep. of Germany. | |
| 3302089 | 7/1984 | Fed. Rep. of Germany. | |
| 2717089 | 10/1984 | Fed. Rep. of Germany. | |

Primary Examiner—Daniel M. Yasich
Attorney, Agent, or Firm—Mason, Fenwick & Lawrence

[57] ABSTRACT

The optoelectronic interface and refractive index display device has a light-emitting diode the light from which is fed through an optical waveguide to a sensing element. A planoconvex lens collimates the light which then passes through a regular cylindrical element to a circular cone. Total reflection occurs at the lateral conical surface thereof when the circular cone is in a gaseous atmosphere. The reflected light is fed through the regular cylindrical element, the planoconvex lens, and then through a common waveguide and receiving waveguide to a photodiode. When the circular cone is immersed wholly or partially in liquid, the light coupled into the sensing element experiences no significant total reflection. The signal generated by photodiode decreases accordingly. The planoconvex lens reduces signal loss.

10 Claims, 1 Drawing Sheet

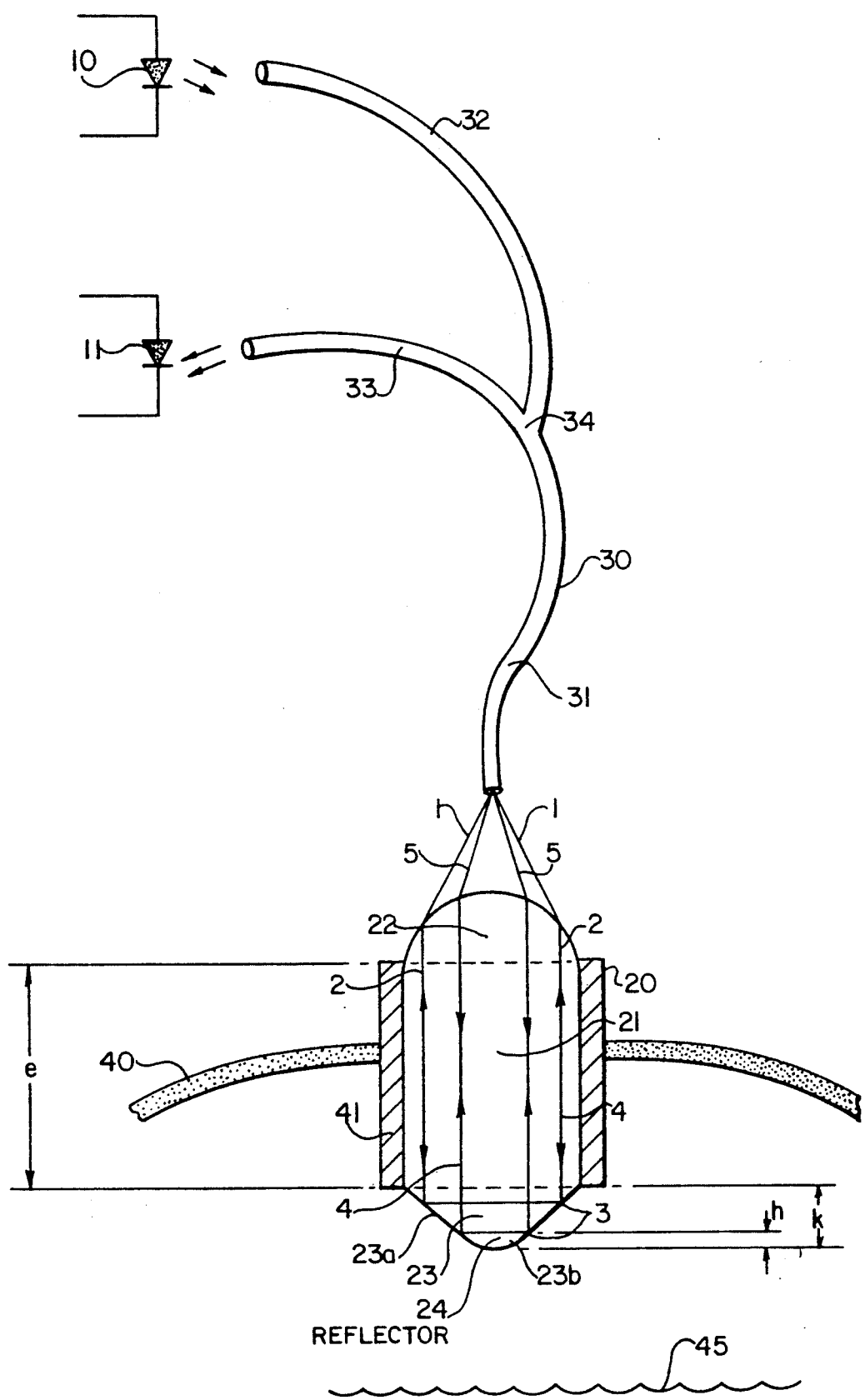
REFLECTOR

DEVICE FOR OPTOELECTRONIC INTERFACE MEASUREMENT AND REFRACTOMETRY IN LIQUIDS

BACKGROUND OF THE INVENTION

The invention relates to a device for optoelectronic interface measurement and refractometry in liquids.

Interface measurement and refractometry and/or display devices of this kind are used for example to measure fullness or to monitor the liquid boundary layer between two immiscible liquids of different densities in explosion-prone tanks, e.g. liquefied gas tanks or containers of solvents or the like, with the level of a liquid interface being determined from the change in the refractive index at the transition between the liquids. In this case, the electrical or electronic control devices must be located outside the explosion-prone area. The signal that monitors the liquid level is therefore generated in the explosion-prone area exclusively by optical means, then transmitted and modulated, with electrical evaluation being performed at a location remote from the liquid container.

These interface or refractive index display or measuring devices have a sensor located above the surface of the liquid, to which light is fed from at least one light source through optical waveguides and whose interface, as long as it remains above the liquid medium, partly reflects the coupled light due to total reflection. The reflected light is in turn fed to a photodetector through an optical waveguide. However, if the sensing element, made of transparent glass or plastic, comes in contact with the surface of the liquid, a portion of the light striking the interface will fall below the total reflection angle as a function of the refractive index of the medium and be decoupled into the liquid, with only a small amount reaching the photodetector.

Offenlegungsschrift DE 33 02 089 A1 teaches a system suitable for this purpose wherein the light is guided through multimode optical waveguides by total internal reflection.

One key disadvantage of this arrangement is that the signal deflection, i.e. the signal differential, between the value measured when the sensor is not wet and the value when it is wet is comparatively small. This means that many of the light modes guided in the optical waveguide and reflected many times at the inside wall of the waveguide escape from the boundary layer upon contact with air because they fall below the total reflection angle. Even when the sensing element is wetted by the liquid, disturbing reflections that reduce signal deflection can be expected, sharply reducing the potential sensitivity (difference in refractive index with respect to the liquid, change in degree of reflection).

The goal of the present invention is to provide an optoelectronic device of the type described, especially for monitoring explosion-prone liquids, said device avoiding the above noted disadvantages while ensuring maximum possible signal defection.

SUMMARY OF THE INVENTION

The present invention provides a sensing element having a planoconvex lens to collimate the light fed to the cylindrical part of the sensing element through optical waveguides, feeding the light through the regular cylindrical element without significant reflection at the cylindrical wall to a conical interface, rounded at the tip in the shape of a cap, where it is deflected in the case of partial or total reflection and guided parallel to the cylindrical wall back to the planoconvex lens. The lens focuses the collimated light on the return optical waveguide which feeds the coupled light, mostly unattenuated apart from reflection and scattering losses, to the photodetector. If the conical interface is wetted by a liquid, however, by the surface of the liquid to be monitored for example, a certain portion of the light passes through the interface into the liquid medium so that only a very specific part reaches the photodetector. Then the difference between the refractive indices of the sensing element and the medium determines the total reflection angle and hence the area of the sensor tip, shaped like a rounded cap, at which total reflection occurs. Hence, only a portion of the light striking the entire sensing element tip interior is reflected back. This portion of the light is directly proportional to the difference in refraction between the medium and the liquid. Quantitative evaluation of the totally reflected light component thus permits determination of the refractive index of the liquid wetting the sensing element tip and permits its use as a refractometer.

The sensing element with its cylindrical planoconvex lens and circular cone can consist of one piece of transparent glass or plastic. The light can be guided to and from it either by separate optical waveguides or by a Y-shaped branched optical waveguide.

When using the construction of the invention to display the interface and refractive index in an explosion-prone environment, regulations for protection against flame penetration can be met very simply by appropriately dimensioning the length of the cylindrical element of the sensor. Complicated and therefore expensive solutions (cf. DE-GM 79 08 489) for bringing out the fiber bundle can be avoided by connecting the optical waveguides to the sensing element on the unpressurized side of the container.

The subject of the invention will be explained below.

BRIEF DESCRIPTION OF THE DRAWING

The single FIGURE of the drawing is a partly schematic view, with parts in cross section, of a device for optoelectronic interface measurement and refractometry in liquids in accordance with the present invention.

In this embodiment, the device according to the invention is used to monitor the interface between separate immiscible liquids 45 stratified as a function of their physical density.

This function is achieved by sensing element 20 which passes through the wall 40 of a container, not shown in detail, by its regular cylindrical central part 21 and is sealed off from the latter in a liquid- and gas-tight manner by a gasket 41 shown schematically. The light 1, 5 to be coupled into and out of sensing element 20 is fed in and out through waveguide system 30 comprising optical waveguides 31 to 33.

A light-emitting diode [LED] 10 or another semiconductor component that emits light can be used as the light source for example, and a photodiode 11 or similar photosensor can be used as the photodetector. The light generated by LED 10 is conducted through transmitting optical waveguide 32 and branch 34 to common optical waveguide 31, from whose end the still uncollimated light 1 emerges. This light 1 is collimated by a planoconvex lens 22 of sensing element, as indicated by beams 2, and fed in this form through regular cylindrical element 21 of sensing element 20 without significant reflection at the cylinder walls. The end of sensing element 20 that is directed toward the surface of liquid 45 is in the form of a circular cone 23, with a circular cone height k that terminates at one end in a rounded cap 24 with a cap height h, said cap having the shape of a spherical skull cap for example, with the conical lateral surface 28 of said cap forming the interface. The curvature of cap 24 is dimensioned so that in contact with air or a comparable gaseous atmosphere, a large portion of collimated light 2 is totally reflected at surface or interface 23a in the direction of light beams 3 and 4 so that it returns parallel to planoconvex lens 22. The lens collimates the emerging light in the direction of beams 5 so that the reflected light is fed through joint waveguide 31, passes through branch 34 to receiving light guide 33, and is fed from the latter to photodiode 11 with only minor loss. Of course, the beam path is highly schematicized by arrows 1 to 5; the arrows drawn on the beam path could also be directed in the other direction, depending on the how the light enters and leaves.

However, if surface or interface 23a is in contact with, i.e., wetted by the liquid, i.e. if it is immersed wholly or partially in elevated liquid 45, collimated light 2 emerges with a circumference determined by the difference in the refractive index between the sensing element and the medium, so that only a portion of the light is returned in the direction of arrows 4. A portion of the light which is suitable for distinguishing different refractive indexes reaches photodiode 11 which acts as a photodetector.

I claim:

1. Apparatus for optoelectronic interface in and for refractometry in liquids comprising:

light transparent sensing means for sensing liquid level comprising a generally cylindrical part, means for introducing collimated light into one end of said cylindrical part, and reflecting means optically coupled with said cylindrical part at the opposite end thereof comprising a circular cone having a base for receiving light from and transmitting light to said cylindrical part and having a conical lateral surface for providing an interface between said cone and a liquid medium when liquid medium reaches a level to wholly or partially immerse said conical lateral surface and for thereupon reflecting a first amount of collimated light into said cylindrical part, and for reflecting a different amount of light into said cylindrical part when said conical lateral surface is in contact with a different medium; and means for receiving and measuring the amount of light passed into said cylindrical part from said reflecting means.

2. The apparatus of claim 1, wherein said means for introducing collimated light comprises lens means at said one end of said cylindrical part for receiving light from a light source and for collimating said light.

3. The apparatus of claim 1, said lens means comprising a planoconvex lens at said one end of said cylindrical part.

4. The apparatus of claim 1, said cone being terminated by a rounded cap.

5. The apparatus of claim 4, wherein said rounded cap has a height approximately one-third of the total height of said circular cone.

6. The apparatus of claim 1, said light introducing means comprising means for emitting light, lens means for collimating light, and at least one optical waveguide extending between said light emitting means and said lens means.

7. The apparatus of claim 6, and an optical waveguide extending between said lens means and said light receiving means.

8. The apparatus of claim 7, said waveguides comprising a first branch adjacent said lens means, and branches leading to said light emitting means and said light receiving means.

9. The apparatus of claim 1, said collimated light introducing means comprising lens means for collimating light integral with said sensing element, said reflecting means comprising a cone integral with said sensing element.

10. The apparatus of claim 1, and a container having a wall, said sensing element extending through said wall and having a predetermined length prescribed for protection against flame penetration.

* * * * *